(12) United States Patent
Fischell et al.

(10) Patent No.: US 6,534,693 B2
(45) Date of Patent: Mar. 18, 2003

(54) SURGICALLY IMPLANTED DEVICES HAVING REDUCED SCAR TISSUE FORMATION

(75) Inventors: Robert E. Fischell, Dayton, MD (US); David R. Fischell, Fair Haven, NJ (US); Tim A. Fischell, Richland, MI (US); Scott J. S. Fischell, Glenelg, MD (US)

(73) Assignee: Afmedica, Inc., Kalamazoo, MI (US)

( * ) Notice: Subject to any disclaimer, the term of this patent is extended or adjusted under 35 U.S.C. 154(b) by 0 days.

(21) Appl. No.: 09/772,693

(22) Filed: Jan. 31, 2001

(65) Prior Publication Data

US 2002/0055701 A1 May 9, 2002

Related U.S. Application Data

(63) Continuation-in-part of application No. 09/705,999, filed on Nov. 6, 2000.

(51) Int. Cl.[7] ............................................... A61F 13/00
(52) U.S. Cl. .......................................... 602/43; 602/48
(58) Field of Search ...................... 606/151; 424/78.01, 424/422, 427, 428; 514/912.44; 623/66; 128/898; 602/41, 43, 46; 604/890.1, 891.1, 304

(56) References Cited

U.S. PATENT DOCUMENTS 4,863,457 A * 9/1989 Lee ......................... 604/294 X
4,865,031 A * 9/1989 O'Keeffe .................... 606/151

(List continued on next page.)

FOREIGN PATENT DOCUMENTS

WO  WO01/87372  11/2001  ........... A61L/31/61

OTHER PUBLICATIONS

U. S. patent application Ser. No. 09/850,365, Falotico et al., filed May 7, 2001.
U. S. patent application Ser. No. 09/771,480, Helmus et al., filed Jan. 25, 2001.

(List continued on next page.)

*Primary Examiner*—Nicholas D. Lucchesi
*Assistant Examiner*—Lalita M. Hamilton

(57) ABSTRACT

This invention is an anti-proliferative drug placed onto or within a sterile sheet or mesh that is designed to be placed between internal body tissues to prevent the formation of post-operative adhesions, which adhesions are really scar tissue formation. This mesh or gauze onto or into which the drug is placed may be either a permanent implant or it may be biodegradable. By impregnating an existing product such as the Johnson & Johnson SURGICEL™ absorbable hemostat gauze-like sheet with an anti-proliferative drug such as Rapamycin or Taxol, the biodegradable, drug impregnated mesh would act as a barrier to cell proliferation and hence be a deterrent to the formation of adhesions. Another embodiment of this invention is an anti-proliferative drug attached to a bandage that is placed onto a cut in the skin to decrease scar tissue formation. Still another embodiment of the invention is an anti-proliferative drug that is attached to a surgical suture or coated onto a surgical staple both of which are used for connecting human tissues. The suture or staple then being more capable for decreasing cellular proliferation where the suture or staple material passes through the human tissue.

21 Claims, 1 Drawing Sheet

U.S. PATENT DOCUMENTS

| | | | | |
|---|---|---|---|---|
| 4,895,566 A | | 1/1990 | Lee | 604/266 |
| 4,952,403 A | * | 8/1990 | Vallee | |
| RE33,375 E | | 10/1990 | Luck et al. | 514/2 |
| 5,151,413 A | | 9/1992 | Caufield et al. | 514/63 |
| 5,387,589 A | | 2/1995 | Kulkarni | 514/291 |
| 5,496,832 A | | 3/1996 | Armstrong | 514/291 |
| 5,516,781 A | * | 5/1996 | Morris et al. | 514/291 |
| 5,540,931 A | | 7/1996 | Hewitt | |
| 5,552,162 A | * | 9/1996 | Lee | |
| 5,618,553 A | * | 4/1997 | Kelleher | 424/428 |
| 5,624,893 A | | 4/1997 | Yanni | 514/2 |
| 5,693,607 A | * | 12/1997 | Segarini | |
| 5,708,002 A | | 1/1998 | Luly et al. | 514/291 |
| 5,756,673 A | | 5/1998 | Sonnenshein et al. | 530/350 |
| 5,795,286 A | * | 8/1998 | Fischell et al. | 600/3 |
| 5,798,334 A | * | 8/1998 | Cutroneo | |
| 5,843,156 A | | 12/1998 | Slepian et al. | 128/898 |
| 5,912,224 A | | 6/1999 | Donahoe et al. | 514/2 |
| 5,912,253 A | | 6/1999 | Cottens et al. | 514/291 |
| 5,981,568 A | | 11/1999 | Kunz et al. | 514/411 |
| 6,015,815 A | | 1/2000 | Mollison | 514/291 |
| 6,060,474 A | * | 5/2000 | Williams | |
| 6,063,396 A | | 5/2000 | Kelleher | 424/428 |
| 6,117,425 A | | 9/2000 | MacPhee et al. | 424/94.64 |
| 6,124,273 A | | 9/2000 | Drohan et al. | 514/55 |
| 6,143,037 A | * | 11/2000 | Goldstein et al. | 623/66 |
| 6,200,985 B1 | | 3/2001 | Cottens et al. | 514/291 |
| 6,221,099 B1 | * | 4/2001 | Anderson et al. | 623/1.15 |
| 6,273,908 B1 | * | 8/2001 | Ndondo-Lay | 623/1 |

OTHER PUBLICATIONS

U. S. patent application Ser. No. 09/850,293, Falotico et al., filed May 7, 2001.

U. S. patent application Ser. No. 09/850,232, Falotico et al., filed May 7, 2001.

U. S. patent application Ser. No. 09/850507, Falotico et al., filed May 7, 2001.

U. S. patent application Ser. No. 09/850,233, Falotico et al., filed May 7, 2001.

U. S. patent application Ser. No. 09/850,482, Falotico et al., filed May 7, 2001.

* cited by examiner

SURGICALLY IMPLANTED DEVICES HAVING REDUCED SCAR TISSUE FORMATION

REFERENCE TO A PREVIOUS PATENT APPLICATION

This is a continuation-in-part application of the patent application Ser. No. 09/705,999 filed on Nov. 6, 2000.

FIELD OF USE

This invention is in the field of materials used to prevent the formation of scar tissue subsequent to a surgical procedure or accidental skin cut of a human subject.

BACKGROUND OF THE INVENTION

Post-operative adhesions are a major problem following abdominal and other surgical procedures. These adhesions are caused by the unwanted proliferation of scar tissue between internal tissues and structures of the human body generally after surgery. Several companies have developed sheets of biodegradable mesh that can be placed between these structures to reduce the tissue growth. None are entirely effective as some scar tissue typically grows through the mesh. U.S. Pat. No. 5,795,286 describes the use of a beta emitting radioisotope to reduce the proliferation of tissue through a biocompatible material placed into the human body. Although radioisotopes may be effective at preventing the cell proliferation associated with adhesions, the limited shelf life and safety issues associated with radioisotopes makes them less than ideal for this purpose.

Recent publications (Transcutaneous Cardiovascular Therapeutics 2000 Abstracts) report a greatly reduced cell proliferation within angioplasty injured arteries when vascular stents used for recannalization are coated with an anti-proliferative drug such as Rapamycin (Sirolmus) or Taxol. However, these drugs have never been used for reducing cellular proliferation of tissues separated by a surgical procedure.

SUMMARY OF THE INVENTION

A first embodiment of this invention is a device consisting of a drug impregnated into, coated onto or placed onto a material sheet or mesh designed to be placed between internal body tissues that have been surgically separated to prevent the formation of post-operative adhesions, which adhesions are really scar tissue formation. A drug that is impregnated into a gauze-like material or coated onto the material or joined to the material by adhesion and/or capillary action is defined herein as a drug "attached" to a mesh. This mesh or gauze onto which the drug is attached may be either a permanent implant or it may be biodegradable. The drug can be attached to an existing product such as the Johnson & Johnson SURGICEL™ absorbable hemostat gauze-like sheet. With an anti-proliferative drug such as Rapamycin or Taxol which have a known effect on proliferating cells, the biodegradable mesh would decrease cellular proliferation and hence be a deterrent to the formation of adhesions. It is also envisioned that an anti-proliferative drug attached to a bandage could be placed onto a cut in the skin for reducing scar tissue formation. This cut could be accidental or a result of a surgical incision. It is also envisioned that an anti-proliferative drug could be attached to surgical suture material that is used (for example) to join together two blood generally cylindrical cavitys, i.e., an anastomosis, with the attached drug causing a reduction in cellular proliferation in the vicinity where the sutures penetrate through the human tissue. It should be understood that the suture material could be either soluble or insoluble and could be used for any application for which sutures are used. Still another embodiment of the present invention is an anti-proliferative drug coated onto a surgical staple thus reducing scar tissue around that staple. Still another embodiment of this invention is to attach an anti-proliferative drug to a device such as a buckle that is used for the treatment of a detached retina. Since scar tissue formation is one of the main complications of a retinal attachment procedure, by attaching an anti-proliferative drug to the buckle that is placed around the eye, there can be some reduction in scar tissue formation. It is also envisioned to attach an anti-proliferative drug attached to the outside of a cylindrical tube that is placed within a generally cylindrical cavity of the human body to decrease scar tissue formation after a surgical procedure on that generally cylindrical cavity. Such a generally cylindrical cavity might be a nostril after an operation for a deviated septum, a fallopian tube, a billiary duct, a urethra, (for example after prostate surgery) a ureter, a bronchial tube, etc. For such an application, the tube with the attached anti-proliferative drug could be biodegradable, remain implanted or it could be removed after a few days or weeks.

Another device that would benefit from a coating of an anti-proliferative agent such as Rapamycin is a prosthetic implant that is placed into a woman's breast after reconstructive or augmentative surgery. Breast implants typically form significant scar tissue around their surface after implantation. Coating the surface of the breast implant with a slowly releasing anti-proliferative agent can significantly reduce this scar tissue formation.

Still another application of these concepts is for ateriovenous fistulas that are used for kidney dialysis patients. These devices (which are also called a-v shunts) are used to connect an artery in an arm to a large vein in the same arm. The plastic a-v shunt is then penetrated by comparatively large needles through which the patient's blood is cleansed typically every other day. A frequent cause of failure for these shunts is caused by proliferative cell growth at the anastamosis where the shunt is joined to a vein. By having sutures coated with an anti-proliferative agent and by coating the interior and/or exterior of the a-v shunt with an anti-proliferative agent it is expected that the time for maintaining adequate blood flow through the vein will be extended.

In addition to applying the anti-proliferative drug by means of a device to which the anti-proliferative drug is attached, it is also envisioned to apply the anti-proliferative drug systemically by any one or more of the well known means for introducing a drug into a human subject. For example, an anti-proliferative drug could be applied by oral ingestion, by a transdermal patch, by a cream or ointment applied to the skin, by inhalation or by a suppository. Any of these methods being a systemic application of an anti-proliferative drug. It should be understood that such a drug should be applied systemically starting at least one day prior to a surgical procedure but could be started as long as 5 days prior to a surgical procedure. Furthermore, the drug should be applied for a period of at least one day after the procedure and for some cases as long as 60 days. It should be understood that an anti-proliferative drug could be given systemically without using any of the devices described herein. Preferably, the anti-proliferative drug would be given systemically in addition to the application of an anti-proliferative drug attached to any one or more of the devices described herein. It should also be understood that an optimum result might be obtained with using one anti-proliferative drug attached to a device with a second and/or third drug being used for systemic administration. A typical dose for a patient, for example with Rapamycin, would be 1.5 mg/kg per day. The dose would of course depend on the anti-proliferative drug that was used.

Thus it is an object of this invention to have a sheet of material that can be placed between internal body tissues, the material having an anti-proliferative drug attached to reduce scar tissue formation between adjacent layers of the human tissue.

Another object of this invention is to have a biodegradable sheet of material or mesh suitable for placement between body tissues including an attached drug that prevents the cellular proliferation associated with post-surgical adhesions.

Still another object of the invention is to have a bandage to which an anti-proliferative drug is attached that is placed onto a cut in the skin to reduce scar tissue formation.

Still another object of the invention is to have a suture material or surgical staple to which an anti-proliferative drug is attached.

Still another object of the invention is to have an anti-proliferative drug attached to the exterior of a cylindrical tube that is placed into a generally cylindrical cavity of the human body after a surgical procedure on that generally cylindrical cavity.

Still another object of the invention is to have a device implanted in a human subject, the device having an anti-proliferative agent attached; the device being a breast implant, an a-v shunt or an equivalent device for implantation into the human subject.

Still another object of this invention is to have the anti-proliferative drug be Rapamycin or an equivalent drug.

Still another object of this invention is to have the anti-proliferative drug be Taxol or an equivalent drug.

Still another object of the invention is to employ a device placed into or onto the body of a human subject, which device has an attached anti-proliferative drug, plus using the same or a different anti-proliferative drug as a medication to be applied systemically to the human subject from some time prior to a surgical procedure to some time after that procedure.

These and other objects and advantages of this invention will become obvious to a person of ordinary skill in this art upon reading of the detailed description of this invention including the associated drawings.

DETAILED DESCRIPTION OF THE DRAWINGS

Figure 1:
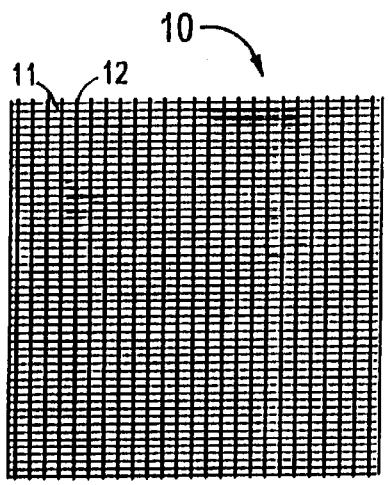
FIG. 1 is a plan view of a sheet or mesh onto which an anti-proliferative drug has been attached.

FIG. 1 shows an absorbable hemostat mesh sheet 10 with mesh strands 12 and open spaces 11. The sheet 10 is designed to be placed post-operatively between internal body tissues that have been separated by a surgical procedure. The mesh strands 12 can be made from oxidized regenerated cellulose or other biodegradable materials with the anti-proliferative drug either embedded within the strands, coated onto the outer surfaces of the strands or held onto the strands by adhesion or capillary action. Any of these possibilities will be described herein as the drug being attached to the mesh or attached to the strand of the mesh.

Figure 2:
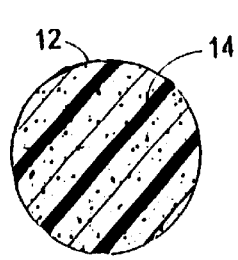
FIG. 2 is an enlargement of the cross section of a single strand of the mesh where the drug is embedded within the strand.

FIG. 2 is an enlargement of a cross section of a single strand 12 of the mesh 10 in which the anti-proliferative drug 14 is embedded within the strand 12.

Figure 3:
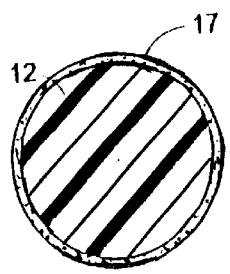
FIG. 3 is an enlargement of the cross section of a single strand of the mesh where the drug is coated onto the strand.

FIG. 3 is an enlargement of the cross section of a single strand 12 of the mesh where the anti-proliferative drug 17 is coated onto the exterior surface of the strand.

Figure 4:
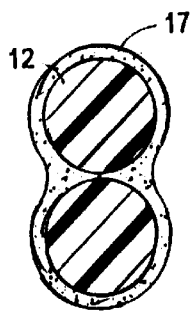
FIG. 4 is an enlargement of two strands of the mesh that have been dipped into a solution of an anti-proliferative drug thereby attaching the drug to the strands by adhesion and capillary action.

FIG. 4 is an enlargement of two adjacent strands 12 of the mesh 10 onto which an anti-proliferative drug 18 is attached by means of adhesion and capillary action.

Figure 5:
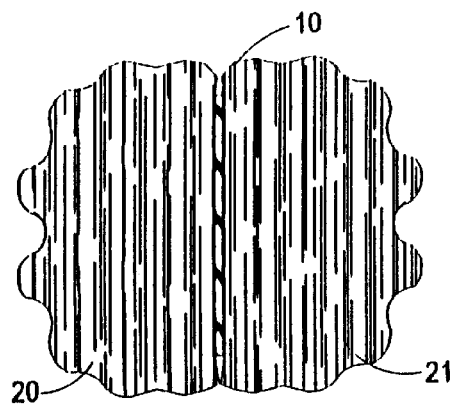
FIG. 5 shows a cross section of the mesh to which an anti-proliferative drug has been attached, the mesh being placed between two layers of tissue of the human body.

FIG. 5 shows the anti-proliferative drug attached to the mesh 10 placed between two adjacent tissues 20 and 21 of a human body. The mesh 10 would be inserted during a surgical procedure typically just before closing of the surgical incision. When the biodegradable mesh 10 dissolves or is absorbed into the tissues 20 and 21, the anti-proliferative drug attached to the mesh 10 will become dispersed into the tissues 20 and 21. On the other hand, if the biocompatible sheet of material is not biodegradable, the anti-proliferative drug will remain at the site where it is placed for a longer period of time than if the material sheet is biodegradable. Similarly, the drug itself may be produced in a soluble or insoluble form. An insoluble form would remain at the treatment site longer than a soluble form.

The anti-proliferative drugs that may be used include cancer drugs such as Taxol and other known anti-proliferative drugs such as Rapamycin. Other drugs that could be used are Alkeran, Cytoxan, Leukeran, Cis-platinum, BiCNU, Adriamycin, Doxorubicin, Cerubidine, Idamycin, Mithracin, Mutamycin, Fluorouracil, Methotrexate, Thoguanine, Toxotere, Etoposide, Vincristine, Irinotecan, Hycamptin, Matulane, Vumon, Hexalin, Hydroxyurea, Gemzar, Oncovin and Etophophos, taclolimus (FK506), and the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

Although a mesh has been discussed herein, more generally, an anti-proliferative drug can be made to be part of any sheet of material that is or is not biodegradable, as long as the sheet of material is biocompatible. In any case the effect of the anti-proliferative drug that is attached to at least part of the sheet of material will decrease cellular proliferation and therefore decrease the formation of scar tissue and adhesions.

It should also be understood that the mesh 10 could be rolled into a cylinder and placed into a generally cylindrical cavity of the human body that has undergone a surgical procedure. The mesh 10, in a cylindrical form, could also be placed around an elastomer tube prior to placement in the human generally cylindrical cavity.

Figure 6:
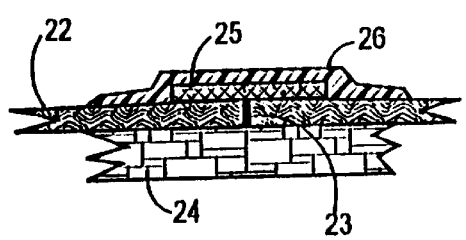
FIG. 6 is a cross section of the skin onto which is taped a bandage to which an anti-proliferative drug has been attached.

FIG. 6 is a cross section of a cut 23 in the skin 22 that is situated above the subcutaneous tissue 24. A bandage 25 to which an anti-proliferative drug has been attached is shown attached to the skin 22 by means of an adhesive tape 26. The purpose of the anti-proliferative drug is to reduce scar tissue formation in order to have an improved appearance of the skin. The bandage may also include an antiseptic agent to decrease the possibility of infection. It should also be understood that an ointment that includes an anti-proliferative agent could be used separately from the bandage 25 of FIG. 6. The anti-proliferative agent would be selected from the group that includes Alkeran, Cytoxan, Leukeran, Cis-platinum, BiCNU, Adriamycin, Doxorubicin, Cerubidine, Idamycin, Mithracin, Mutamycin, Fluorouracil, Methotrexate, Thoguanine, Toxotere, Etoposide, Vincristine, Irinotecan, Hycamptin, Matulane, Vumon, Hexalin, Hydroxyurea, Gemzar, Oncovin and Etophophos, taclolimus (FK506), and the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

Another alternative embodiment of the invention is a suture material to which an anti-proliferative drug is attached. A drawing of a highly enlarged cross section of such a suture would be shown by FIGS. 2 or 3. That is, FIG. 2 could be considered to be a cross section of a suture 12 into which is embedded an anti-proliferative drug 14. FIG. 3 could be considered a highly enlarged cross section of a suture 12 that is coated with an anti-proliferative drug 17. The object of attaching an anti-proliferative drug to a suture would be to reduce scar tissue formation where the suture penetrates through human tissue. This would be particularly true for the use a suture to join together two generally cylindrical cavitys, i.e., an anastamosis. This could be used for both soluble and insoluble suture materials. Furthermore, an anti-proliferative drug could be attached to any surgical staple that is used to join together human tissue after a surgical procedure. It should be understood that sutures or staples with an anti-proliferative agent attached could be used for joining any tissue of a human subject where it is desired to reduce cellular proliferation, i.e., the formation of adhesions or scar tissue.

Figure 7:
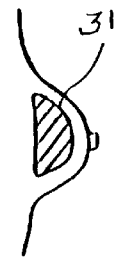
FIG. 7 is a cross section of a human breast into which a breast implant has been placed.

FIG. 7 illustrates the implant into the breast of a human subject of a breast implant 31. Attached to the breast implant 31 would be an anti-proliferative agent selected from the group that includes Rapamycin, Taxol, Alkeran, Cytoxan, Leukeran, Cis-platinum, BiCNU, Adriamycin, Doxorubicin, Cerubidine, Idamycin, Mithracin, Mutamycin, Fluorouracil, Methotrexate, Thoguanine, Toxotere, Etoposide, Vincristine, Irinotecan, Hycamptin, Matulane, Vumon, Hexalin, Hydroxyurea, Gemzar, Oncovin and Etophophos, taclolimus (FK506), and the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline. When a breast implant has an attached anti-proliferative agent, the scar tissue that typically forms around such an implant will be significantly reduced.

If an arterio-venus fistula shunt is placed into the arm of a dialysis patient, then the same type of anti-proliferative agent(s) as described above could be attached to that implanted device to increase the time during which the associated vein in the arm would remain patent.

Figure 8:
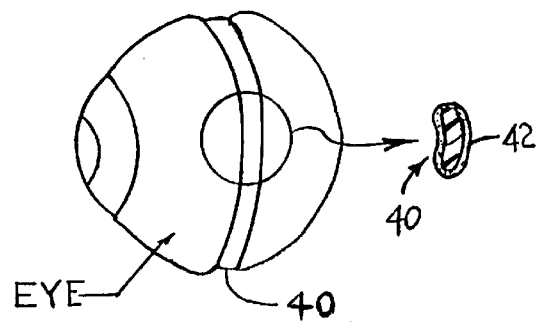
FIG. 8 illustrates a buckle used for the treatment of detached retina.

Another application of the present invention is for prevention of scar tissue formation subsequent to a procedure for attaching a detached retina. This procedure uses what is called a "buckle" placed around the eye to cause re-attachment of the retina. The extent of scar tissue formation after this procedure is performed can be decreased by attaching an anti-proliferative drug to the buckle. FIG. 8 illustrates a buckle 40 having an attached anti-proliferative drug coating 42 that is wrapped around an eye for the treatment of a detached retina. FIG. 8 also shows an enlarged cross section of the buckle 40 with the coating 42 attached on the buckle's outer surface. It should be understood that the anti-proliferative drug could also be contained within the material of the buckle 40.

For any of the applications described herein, the systemic application of one or more of the anti-proliferative agents that have been described could be used conjunctively to further minimize the creation of scar tissue.

Although only the use of certain anti-proliferative agents has been discussed herein, it should be understood that other medications could be added to the anti-proliferative drugs to provide an improved outcome for the patients. Specifically, for applications on the skin, an antiseptic, and/or anti-biotic, and/or analgesic agent could be added to an anti-proliferative ointment to prevent infection and/or to decrease pain. These other agents could also be applied for any other use of the anti-proliferative drugs that are described herein. It is further understood that any human subject in whom an anti-proliferative agent is used plus at least one of the other drugs listed above could also benefit from the systemic administration of one or more anti-proliferative agent that has been listed herein.

Various other modifications, adaptations, and alternative designs are of course possible in light of the above teachings. Therefore, it should be understood at this time that within the scope of the appended claims, the invention can be practiced otherwise than as specifically described herein.

What is claimed is:

1. A sheet of material adapted for implantation between tissues of a human body, the sheet of material including an attached anti-proliferative drug, the anti-proliferative drug being designed to reduce the generation of scar tissue, the anti-proliferative drug being selected from the group consisting of Rapamycin, taclolimus (FK506), and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

2. The apparatus of claim 1 wherein the sheet of material is biodegradable.

3. The apparatus of claim 1 wherein the sheet of material is in the form of a mesh.

4. In combination, including an anti-proliferative drug attached to a bandage for placement over a cut on the skin of a human subject, the anti-proliferative drug being selected from the group consisting of taclolimus (FK506), Rapamycin and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

5. In combination, including an anti-proliferative drug attached to a surgical suture, the suture being adapted to connect human tissue that is separated by a surgical procedure on a human subject, the anti-proliferative drug being selected from the group consisting of taclolimus (FK506), Rapamycin and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

6. In combination, including an anti-proliferative drug attached to a mesh having a generally cylindrical shape for introduction into a generally cylindrical cavity of the human body to decrease scar tissue formation in that generally cylindrical cavity after a surgical procedure on that generally cylindrical cavity, the anti-proliferative drug being selected from the group consisting of taclolimus (FK506), Rapamycin and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

7. The combination of claim 6 wherein the generally cylindrical cavity is a human nostril.

8. A device to reduce scar tissue formation within the eye of a human subject after a retinal attachment procedure, including a buckle designed to be placed onto the eye, the buckle including an attached anti-proliferative, the anti-proliferative drug being selected from the group consisting of taclolimus (FK506), Rapamycin and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

9. An implantable device adapted for surgical implantation within a space within a human body at a location that is external to any vessel of that human body, at least part of the device including an attached anti-proliferative drug, the action of the anti-proliferative drug being a reduction in the generation of scar tissue, the anti-proliferative drug being selected from the group consisting of Rapamycin, taclolimus (FK506), and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

10. The device of claim 9 wherein the device is in the form of a prosthetic breast implant.

11. The device of claim 9 wherein the device is in the form of an arterio-venus fistula shunt.

12. A method for improving the outcome of a surgical procedure, the method being the release into a human subject on whom the surgical procedure has been performed of an anti-proliferative agent in combination with at least one other drug selected from the group consisting of antiseptic agents, anti-biotic agents and analgesic agents, and the anti-proliferative agent being selected from the group consisting of Rapamycin, taclolimus (FK506), and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamy-cin, 32-demethoxy, 2-desmethyl and proline.

13. The method of claim 12 wherein the anti-proliferative agent is used in an ointment that is applied to the skin.

14. The method of claim 12 wherein the anti-proliferative agent is attached to a mesh that is adapted to be placed within the human subject in whom the surgical procedure was performed.

15. The method of claim 12 wherein the anti-proliferative agent is attached to a breast implant.

16. The method of claim 12 wherein the anti-proliferative agent is attached to a suture.

17. The method of claim 12 wherein the anti-proliferative agent is released systemically.

18. A method for decreasing the formation of scar tissue after a surgical procedure, the method comprising the following steps:

a) attaching an anti-proliferative drug onto a sheet of material designed to be placed onto or into a human subject; the anti-proliferative drug being selected from the group consisting of Rapamycin, taclolimus (FK506), and one of the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline; and b) placing the mesh with the attached anti-proliferative drug onto or into a human subject during or after completing a surgical procedure.

19. The method of claim 18 further including the step of systemic application of at least one anti-proliferative drug at least one day prior to the surgical procedure.

20. The method of claim 18 further including the step of a continuing systemic application of at least one anti-proliferative drug for at least one day after the surgical procedure.

21. In combination, an anti-proliferative drug attached to a breast implant, the breast implant being designed to provide breast enlargement for a human female subject, the anti-proliferative drug being selected from the group that includes taclolimus (FK506), Rapamycin and the following analogs of sirolimus: SDZ-RAD, CCI-779, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy, 2-desmethyl and proline.

* * * * *